United States Patent
Megargel et al.

(10) Patent No.: US 11,890,750 B2
(45) Date of Patent: Feb. 6, 2024

(54) SYSTEMS AND METHODS FOR MAIZE EMBRYO PLATING AND REPLATING

(71) Applicants: PIONEER HI-BRED INTERNATIONAL, INC., Johnston, IA (US); E.I. DU PONT DE NEMOURS AND COMPANY, Wilmington, DE (US)

(72) Inventors: Ross Megargel, Johnston, IA (US); Christopher Reppe, Waukee, IA (US); Jacob Patrick Suther, Waukee, IA (US); Jeffrey Dale Wille, Ankeny, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 1493 days.

(21) Appl. No.: 16/092,619

(22) PCT Filed: Apr. 17, 2017

(86) PCT No.: PCT/US2017/027924
§ 371 (c)(1),
(2) Date: Oct. 10, 2018

(87) PCT Pub. No.: WO2017/192257
PCT Pub. Date: Nov. 9, 2017

(65) Prior Publication Data
US 2019/0118392 A1    Apr. 25, 2019

Related U.S. Application Data

(60) Provisional application No. 62/332,646, filed on May 6, 2016.

(51) Int. Cl.
*B25J 15/06*    (2006.01)
*A01H 4/00*    (2006.01)
*H04N 7/18*    (2006.01)

(52) U.S. Cl.
CPC ............ *B25J 15/0616* (2013.01); *A01H 4/00* (2013.01); *A01H 4/001* (2013.01); *H04N 7/181* (2013.01)

(58) Field of Classification Search
CPC ......... B25J 15/06; B25J 15/0616; A01H 4/00; A01H 4/001; H04N 7/181
USPC ........................................................ 209/551
See application file for complete search history.

(56) References Cited

U.S. PATENT DOCUMENTS

| 8,281,935 B2 | 10/2012 | Deppermann |
| 8,916,383 B2 | 12/2014 | Barreiro et al. |
| 9,924,626 B2 | 3/2018 | McCarty, II et al. |
| 11,566,252 B2 | 1/2023 | Calabotta et al. |

(Continued)

FOREIGN PATENT DOCUMENTS

| EP | 3806614 A1 * | 4/2021 | ............ B25J 13/088 |
| KR | 20110134623 A * | 6/2010 | |

(Continued)

OTHER PUBLICATIONS

International Search Report and Written Opinion, International Application No. PCT/US2017/027924 dated Nov. 13, 2017.

*Primary Examiner* — Terrell H Matthews

(57) ABSTRACT

Methods and systems are provided for singulating, orienting, and delivering oriented objects (e.g., embryos) to a desired location (e.g., a plate containing a selected medium).

29 Claims, 12 Drawing Sheets

(56) References Cited

U.S. PATENT DOCUMENTS

| | | | |
|---|---|---|---|
| 2008/0041768 A1* | 2/2008 | Rebinsky | F02M 61/1846 209/587 |
| 2010/0124445 A1* | 5/2010 | Tanaka | G03G 15/657 399/308 |
| 2016/0060713 A1 | 3/2016 | Arnold et al. | |

FOREIGN PATENT DOCUMENTS

| | | | |
|---|---|---|---|
| KR | 20140004214 A * | 2/2012 | |
| WO | 2001/013702 A2 | 3/2001 | |
| WO | 2009/126758 A1 | 10/2009 | |
| WO | 2015/134852 A1 | 9/2015 | |
| WO | 2015/171574 A1 | 11/2015 | |
| WO | WO-2017192257 A2 * | 11/2017 | A01G 9/085 |

* cited by examiner

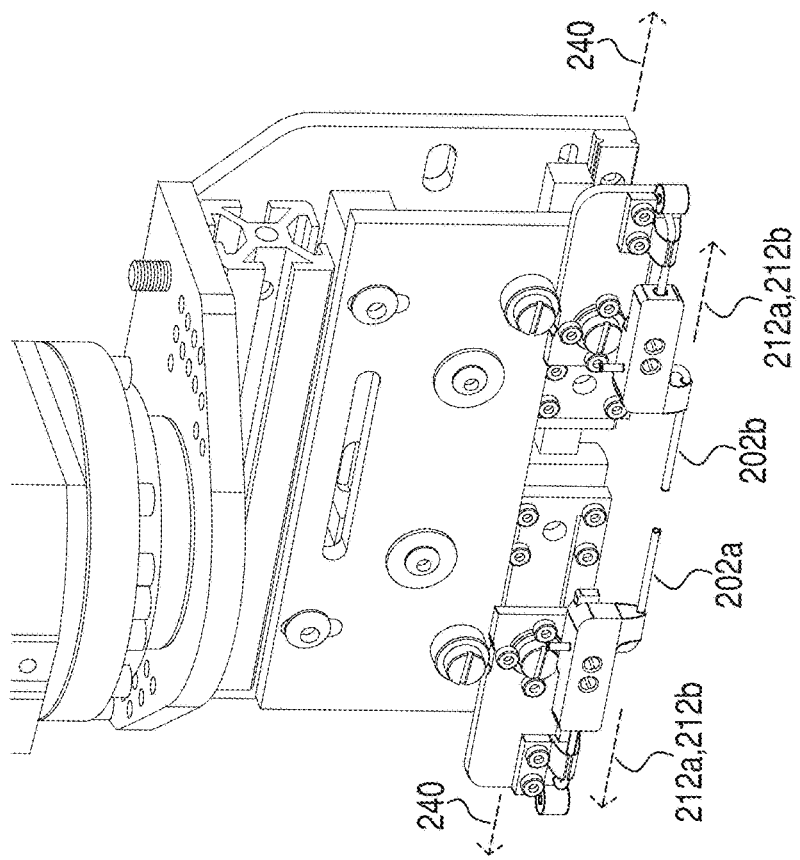
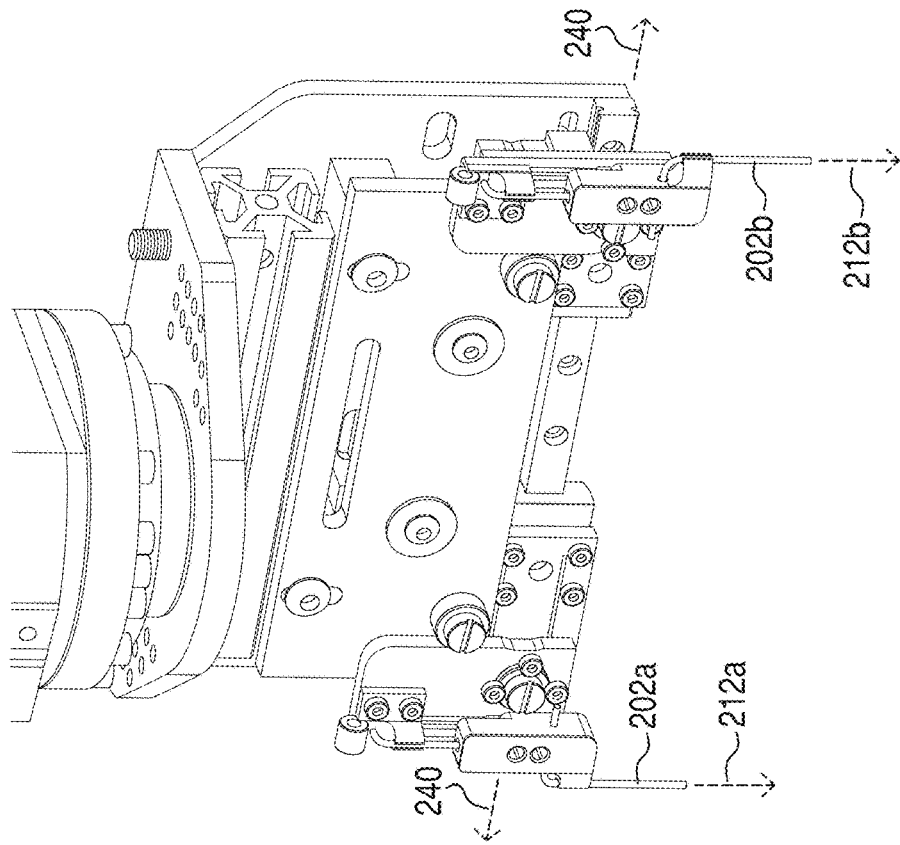

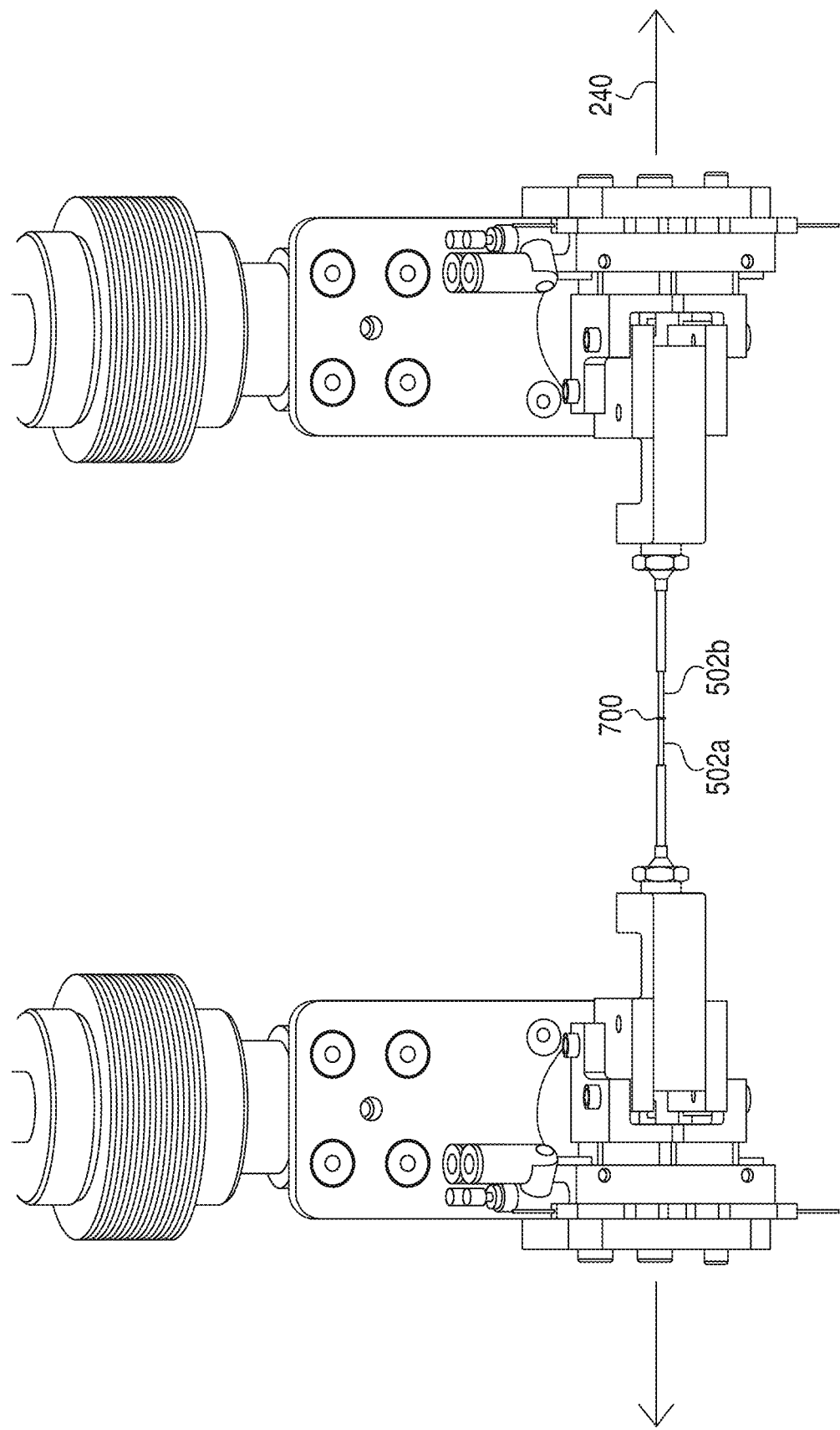

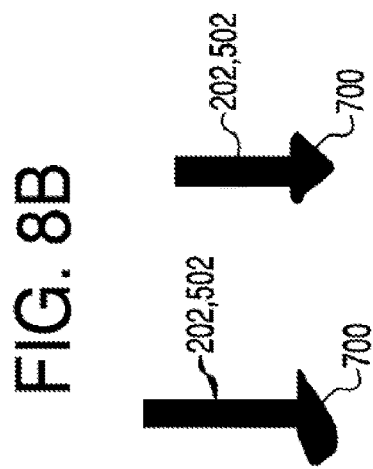
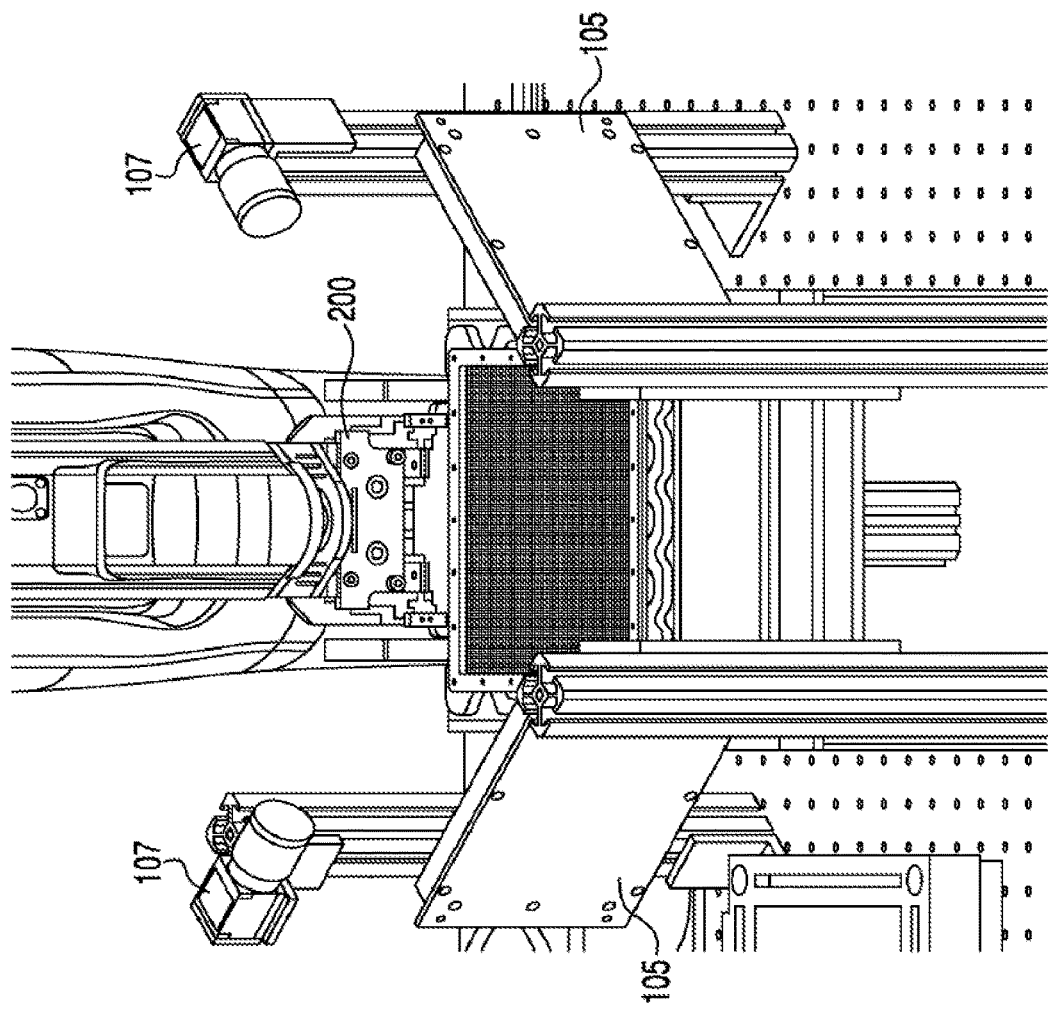

SYSTEMS AND METHODS FOR MAIZE EMBRYO PLATING AND REPLATING

FIELD

The present invention relates generally to systems and methods for positioning objects in a desired orientation and, more particularly, to systems and methods for singulating, orienting, transferring, and/or plating plant embryos.

BACKGROUND

Existing methods for harvesting plant embryos frequently require workers to manually singulate extracted embryos, to manually identify embryos having desired properties, to manually place extracted embryos in a desired orientation, and/or to manually plate extracted embryos within a desired container. For example, during harvesting of corn embryos, extracted embryos may be manually singulated. The singulated embryos can then be manually placed in a first orientation during a chromosome doubling process and may be manually placed in a second, different orientation when contacting a growth medium. Workers can manually select the embryos that should be transferred to the growth medium, and the plating of those selected embryos can be done manually. There is a need for automated systems and methods for accurately and reliably singulating, orienting, transferring, and/or plating extracted embryos.

SUMMARY

Disclosed herein are systems and methods for plating extracted plant embryos. In exemplary aspects, the disclosed systems and methods can be used to singulate, transfer, or orient extracted plant embryos.

In various aspects, disclosed herein is an embryo singulation apparatus having a fluid bath, a screen, an actuator, and a camera. The screen can have a shape configured for receipt within the fluid bath. The actuator can be coupled to the screen and configured to selectively move the screen relative to a vertical axis. The screen can be moveable about and between a submerged position within the fluid bath and an elevated position above the fluid bath. The camera can be positioned above the fluid bath relative to the vertical axis. In use, the camera can be configured to produce an image of embryos on the screen when the screen is in the elevated position above the fluid bath.

Also disclosed are embryo singulation methods including: positioning a plurality of embryos on a screen of the embryo singulation apparatus as disclosed herein; activating the actuator to move the screen to the submerged position within the fluid bath; activating the actuator to move the screen to the elevated position; activating the camera to produce an image of the embryos on the screen; processing the image to identify singulated embryos on the screen; and removing the singulated embryos from the screen.

In various aspects, disclosed herein is an object orientation apparatus having first and second nozzle assemblies. Each of the first and second nozzle assemblies can have a respective vacuum nozzle and a respective actuation subassembly. Each vacuum nozzle can have a respective longitudinal axis and a respective distal end. Each vacuum nozzle can be configured to apply suction to retain an object against the distal end of the vacuum nozzle. Within each nozzle assembly, the vacuum nozzle is rotatable by the actuation subassembly. The vacuum nozzles of the first and second nozzle assemblies are selectively rotatable to an object-transfer position in which the longitudinal axis of the first vacuum nozzle is aligned with the longitudinal axis of the second vacuum nozzle and the distal end of the first vacuum nozzle is positioned proximate the distal end of the second vacuum nozzle. Methods of positioning an object in a desired orientation using the object orientation apparatus are also disclosed. The methods can include: selectively activating at least one actuator of the actuation subassembly of the first nozzle assembly to position the first nozzle assembly in an object release/retrieval position; activating a vacuum source to apply suction through the vacuum nozzle of the first nozzle assembly to retain an object against the distal end of the vacuum nozzle of the first nozzle assembly; producing an image of the object using a camera; and determining an orientation of the object using a controller.

In various aspects, disclosed herein is an object orientation apparatus having a base assembly and first and second nozzle assemblies. The first nozzle assembly can include a first vacuum nozzle. The second nozzle assembly can include a second vacuum nozzle. Each of the first and second vacuum nozzles has a respective longitudinal axis and opposed first and second ends. Each vacuum nozzle can be configured to apply suction to retain an object against the second end of the vacuum nozzle, and each nozzle assembly can be independently rotationally coupled to the base assembly. The first and second nozzle assemblies can be selectively rotatable to an object-transfer position in which the longitudinal axis of the first vacuum nozzle is aligned with the longitudinal axis of the second vacuum nozzle and the second end of the first vacuum nozzle is positioned proximate the second end of the second vacuum nozzle. Methods of positioning an object in a desired orientation using the object orientation apparatus are also disclosed. The methods can include: selectively activating the first rotational actuator and the first transverse actuator to position the first vacuum nozzle in the object release/retrieval position; applying a vacuum force through the first vacuum nozzle to retain an object against the second end of the first vacuum nozzle; producing an image of the object using the camera; and determining an orientation of the object using the controller.

Further disclosed herein is an embryo plating system having an embryo singulation apparatus and an object orientation apparatus as disclosed herein.

BRIEF DESCRIPTION OF THE FIGURES

FIG. 3A depicts the vacuum nozzles of an exemplary object orientation apparatus in respective release-retrieval positions as disclosed herein. FIG. 3B depicts the vacuum nozzles of the object orientation apparatus in respective object-transfer positions as disclosed herein. As further disclosed herein, in the release-retrieval position, each vacuum nozzle can engage an embryo or place an embryo in a desired end location. In the object-transfer position, a first vacuum nozzle (that initially engaged an embryo) can transfer the embryo to a second vacuum nozzle that can then release the embryo at the desired end location.

FIG. 6B is a close-up side perspective view depicting the vacuum nozzles of the first and second nozzle assemblies in an object-transfer position. As shown, the embryo that was retrieved by the first vacuum nozzle assembly is positioned between the vacuum nozzles of the first and second nozzle assemblies.

FIG. 8A is a close-up top perspective view of a system including an object orientation apparatus and a singulation apparatus as disclosed herein. FIG. 8B is a side elevational view of embryos as the embryos are engaged by the distal end of a vacuum nozzle as disclosed herein.

DETAILED DESCRIPTION

Figure 1:
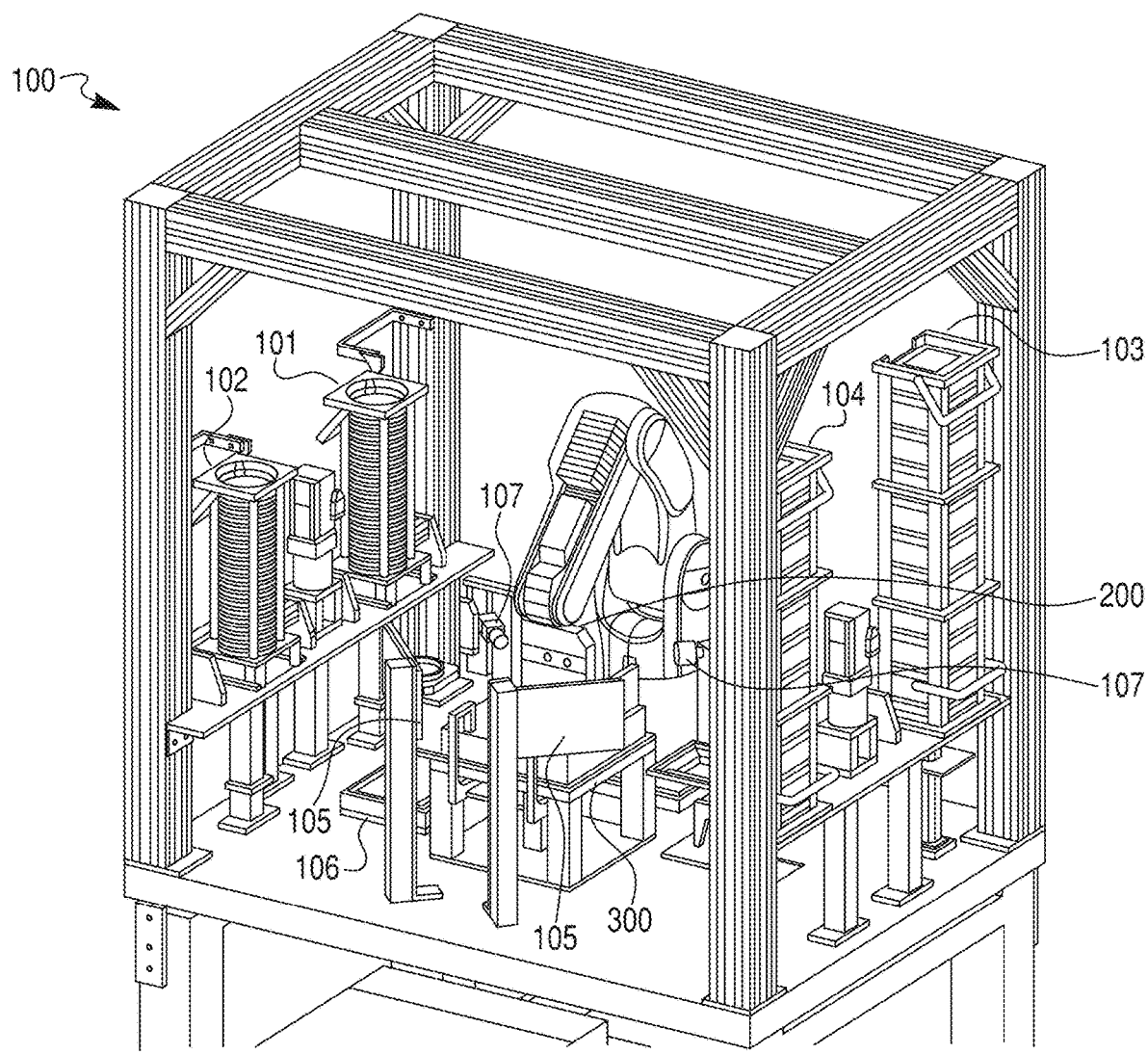
FIG. 1 is a perspective view of an exemplary system for singulating, orienting, and/or plating embryos as disclosed herein.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a", "an", and "the" include plural referents unless the context clearly dictates otherwise. Thus, for example, reference to "an actuator" can include a plurality of such actuators, and so forth.

All technical and scientific terms used herein have the same meaning as commonly understood to one of ordinary skill in the art to which this invention belongs unless clearly indicated otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

I. Overview

The present invention comprises systems and methods for orienting objects (e.g., extracted embryos) in desired orientations for further processing. In exemplary aspects, the disclosed systems and methods can be used to position extracted plant embryos in a desired orientation for contacting a growth medium. Optionally, in these aspects, the disclosed systems and methods can be used to singulate the extracted plant embryos and evaluate the orientation of the singulated embryos to determine if the orientation of the embryos needs to be adjusted to permit further processing. Optionally, the disclosed systems and methods can be used to transport extracted embryos from a first location (e.g., a petri dish or singulation apparatus) to a second location (e.g., a tray containing a growth medium) while ensuring that the embryos are positioned in a desired orientation at the second location. It is contemplated that, unless otherwise stated, any of the steps of the disclosed methods can be performed in an automated fashion.

As used herein, the term "automated" refers to the use of mechanical, electrical, software, imaging, vision-based and/or other known automation-based technologies to augment processes typically performed by human interaction.

In exemplary aspects, it is contemplated that the actuators of the disclosed systems can be positioned in operative communication with at least one controller 800, such as, for example and without limitation, a programmable logic controller (PLC) or a computer having a processor as is known in the art. In these aspects, it is contemplated that the processor of the controller(s) can be configured to activate the actuators of the disclosed systems and assemblies in an automated manner.

II. Systems and Methods of Singulating Extracted Embryos and Other Objects

Figure 7B:
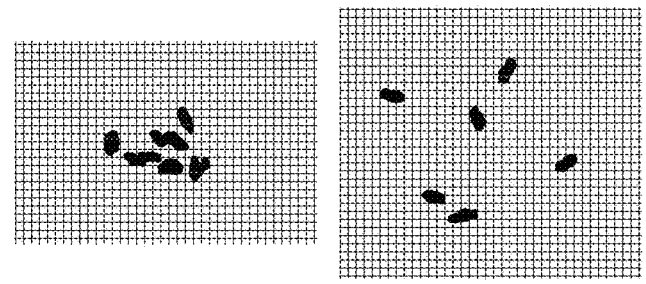
FIG. 7B is a top plan view of a screen of the singulation apparatus following placement of embryos on the screen.
Figure 7A:
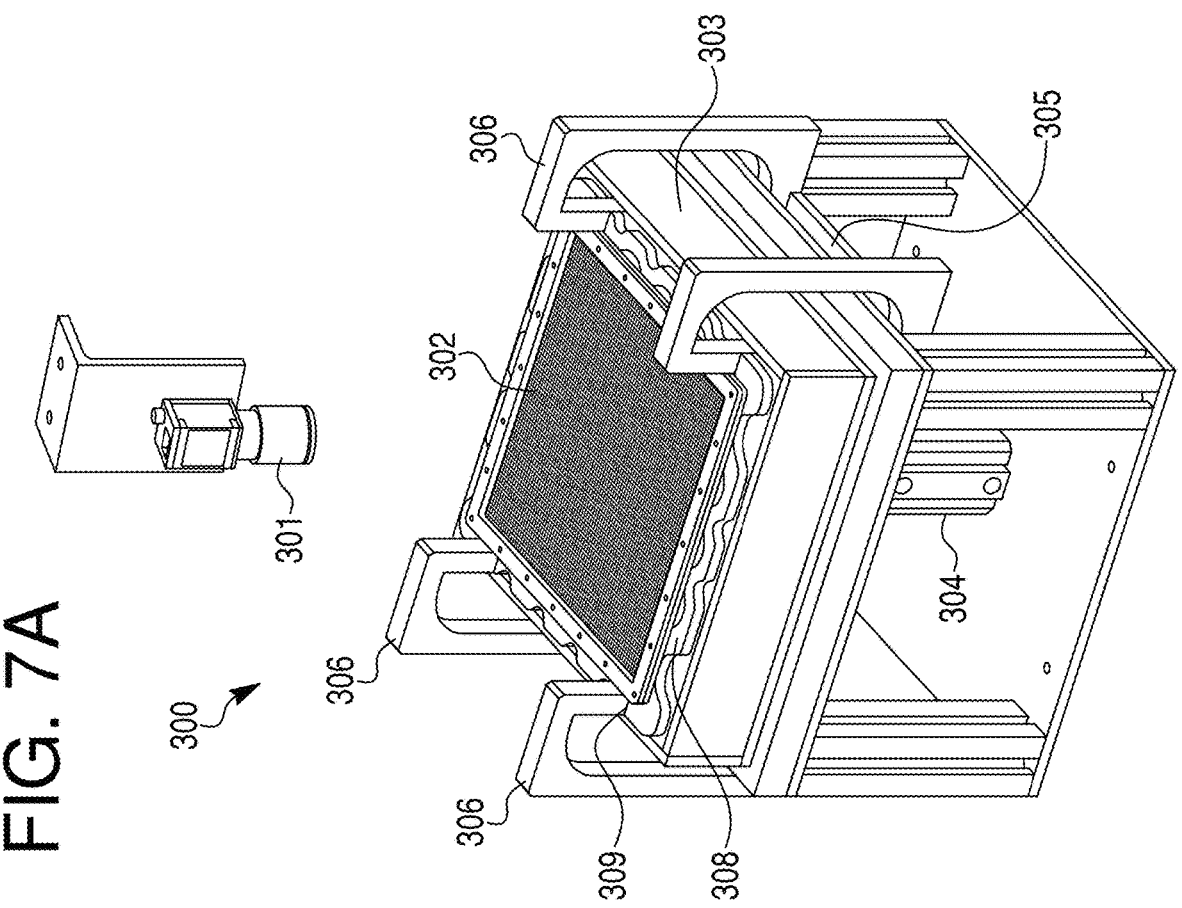
FIG. 7A is a top perspective view of an exemplary singulation apparatus as disclosed herein.

In exemplary aspects, and with reference to FIGS. 1, 7A, and 8A, disclosed herein is a singulation apparatus 300. As further described herein, the singulation apparatus 300 can "singulate" objects (e.g., embryos) to permit processing of individual objects (e.g., embryos), one at a time. In these aspects, the singulation apparatus 300 can comprise a fluid bath 303, a screen 302 having a shape configured for receipt within the fluid bath, at least one actuator 304 coupled to the screen, and a camera 301. In these aspects, the actuator 304 can be configured to selectively move the screen 302 relative to a vertical axis. It is contemplated that the actuator 304 can be a conventional linear actuator, such as, for example and without limitation, a mechanical actuator, a hydraulic actuator, a pneumatic actuator, a piezoelectric actuator, or an electromechanical actuator. In exemplary aspects, the actuator 304 can be a pneumatic cylinder. In other exemplary aspects, the screen 302 can have a mesh structure as is known in the art to permit flow of fluid through the openings defined by the mesh structure. In these aspects, it is contemplated that the mesh structure can have a selected mesh size, such as 20×20 or 40×40 (holes/inch). However, it is contemplated that any desired mesh size can be used, provided the mesh size is large enough to reduce surface tension of an aqueous solution but not so large that the embryo is lodged within or passes through the mesh. In further aspects, the screen 302 can be moveable about and between a submerged position within the fluid bath 303 and an elevated position above the fluid bath. In additional aspects, the camera 301 can be positioned above the fluid bath 303 relative to the vertical axis. In these aspects, when the screen 302 is in the elevated position above the fluid bath, the camera 301 can be configured to produce an image of objects (e.g., embryos) positioned on the screen. Exemplary images of embryos on the screen 302 are shown in FIG. 7B.

In exemplary aspects, the fluid bath can have a substantially rectangular or square perimeter. However, it is contemplated that any desired shape (e.g., a round perimeter shape) can be used. Similarly, it is contemplated that the screen can have any shape that is complementary to the shape of the fluid bath.

As shown in FIG. 7A, it is contemplated that the singulation apparatus 300 can comprise a structure that supports the liquid bath in an elevated position relative to a floor surface or other horizontal surface. Optionally, in exemplary aspects, the support structure can comprise a plurality of support legs extending between the horizontal surface and an undersurface of the fluid bath 303 and/or between the horizontal surface and an undersurface of a platform supporting the fluid bath.

In exemplary aspects, the screen 302 of the singulation apparatus 300 can be positioned on and/or coupled to an upper surface of a support element 308 that is configured for selective movement relative to the vertical axis. In these aspects, the actuator 304 of the singulation apparatus 300 can be coupled to the support element 308 such that the actuator is capable of imparting motion to the support element and, consequently, the screen 302. In exemplary aspects, the actuator 304 can be coupled to the support element 308 by at least one arm 306 that is coupled to the actuator and that extends to the support element. Optionally, in these aspects, the actuator 304 can be coupled to a horizontal platform 305 that is configured for selective movement relative to the vertical axis, and the arms 306 can be coupled to the platform and extend from the platform to the support element 308. In further aspects, the support element 308 can define at least one engagement structure 309 that is configured for selective engagement with the arms. It is contemplated that each engagement structure 309 of the support element 308 can be a recess, a projection, an opening, a slot, or other conventional engagement means that is configured to engage a corresponding portion of an arm 306. Optionally, in some aspects, the arms 306 can be shaped to at least partially extend under the support element 308 to provide additional support and stability to the support element (and the screen 302). For example, as shown in FIG. 7A, when the actuator 304 is positioned below the fluid bath 303, it is contemplated that the arms 306 can have a "C" or "G" type shape, with a distal end of each arm optionally extending underneath a portion of the support element 308. In further exemplary aspects, the support element 308 can comprise at least one opening to allow fluid to reach the screen 302.

In exemplary aspects, the singulation apparatus 300 can further comprise a controller 800 positioned in communication with the camera 301. In these aspects, the controller 800 can comprise a processor configured to analyze the image of the screen 302 produced by the camera 301 to identify singulated embryos on the screen. In one aspect, the processor of the controller 800 can be configured to identify contours of objects (e.g., embryos) on the screen 302 to determine the presence of singulated objects (e.g., embryos) on the screen. In another aspect, the controller 800 can be configured to direct the actuator 304 to move the screen about and between the submerged position and the elevated position.

In use, the singulation apparatus 300 can singulate objects (e.g., previously extracted embryos) for use in downstream processes as further disclosed herein. In exemplary aspects, a method for singulating objects (e.g., embryos) can comprise positioning a plurality of objects (e.g., embryos) on the screen of the singulation apparatus. In these aspects, it is contemplated that the objects (e.g., embryos) can be placed on the screen in either a manual or automated fashion. In another aspect, the method can further comprise activating the actuator to move the screen to the submerged position within the fluid bath. Optionally, in this aspect, the fluid bath can contain an aqueous solution. Optionally, it is contemplated that the liquid bath can be filled with at least one of water, solution, buffer, or liquid gel. In an additional aspect, the method can further comprise activating the actuator to move the screen to the elevated position. In a further aspect, the method can further comprise activating the camera to produce an image of the objects (e.g., embryos) on the screen. In another aspect, the method can further comprise processing the image to identify singulated objects (e.g., embryos) on the screen. In still another aspect, the method can comprise removing the singulated objects (e.g., embryos) from the screen. Optionally, in this aspect, the singulated objects (e.g., embryos) can be removed from the screen by a vacuum nozzle.

In exemplary aspects, the method can further comprise repeating the steps of: activating the actuator to move the screen to the submerged position within the fluid bath; activating the actuator to move the screen to the elevated position; activating the camera to produce an image of the embryos on the screen; processing the image to identify singulated objects (e.g., embryos) on the screen; and removing the singulated objects (e.g., embryos) from the screen until a desired number of singulated objects (e.g., embryos) are removed from the screen. Thus, in use, each time the screen is moved from the submerged position to the elevated position, the processor can identify singulated objects (e.g., embryos) and initiate removal of the singulated objects (e.g., embryos). Then, the process can be repeated as necessary until a desired number of singulated objects (e.g., embryos) have been identified and removed from the screen. In operation, it is contemplated that the objects (e.g., embryos) on the screen will settle to a more singulated state following withdrawal of the screen from the fluid bath.

In exemplary aspects, the processor of the controller can identify singulated embryos on the screen by applying one or more threshold parameters to the image. Such threshold parameters can include size parameters, shape parameters, color parameters, and the like. In various aspects, the processor of the controller can identify singulated embryos in an automated manner by identifying the embryos on the screen and applying the threshold parameters to determine the locations of singulated embryos.

Figure 9:
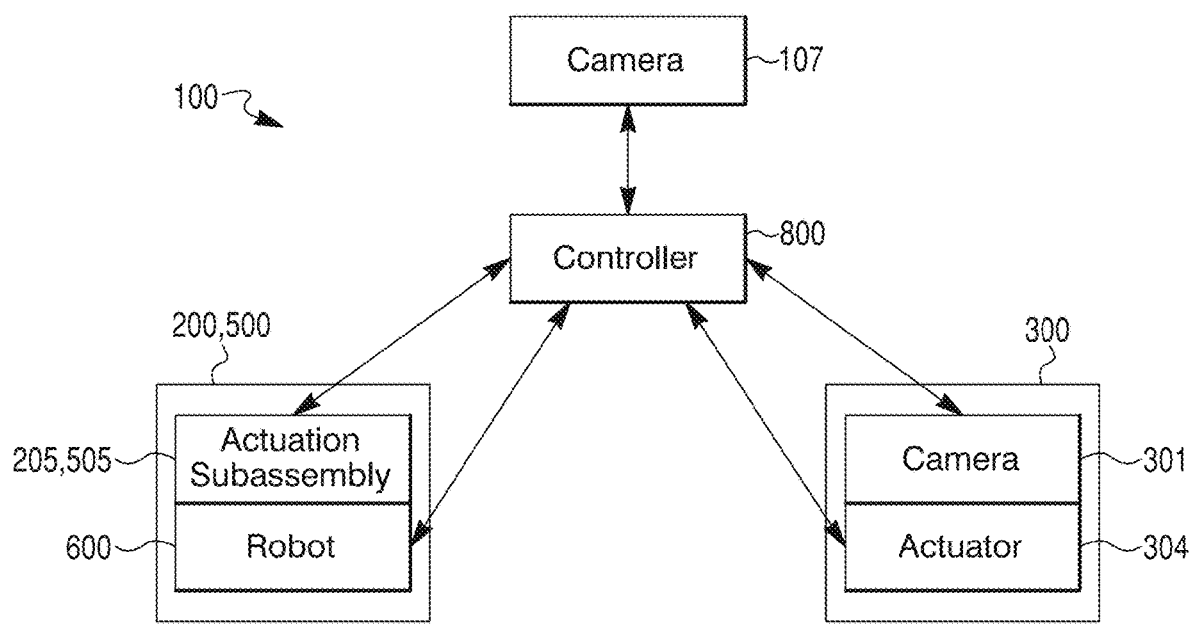
FIG. 9 is a schematic diagram depicting the communication between the at least one controller of the disclosed system and the cameras and actuators within the system.

As shown in FIG. 9, it is contemplated that the at least one controller 800 disclosed herein can function as a central controller of each of the components of the system 100 disclosed herein. However, it is also contemplated that the disclosed singulation apparatus can have its own dedicated controller that can optionally be positioned in communication with other controllers of the system 100.

III. Systems and Methods of Adjusting the Orientation of an Extracted Embryo or Other Object With reference to FIGS. 1-6C, disclosed herein is an object orientation apparatus 200, 500. In exemplary applications, and as further disclosed herein, the object orientation apparatus 200, 500 can be used to position extracted embryos (e.g., plant embryos) in desired orientations. However, it is contemplated that the disclosed object orientation apparatus 200, 500 can also be used to position other objects in desired orientations. In exemplary aspects, the object orientation apparatus can comprise first and second nozzle assemblies 208a, 208b, 508a, 508b.

In exemplary aspects, each of the first and second nozzle assemblies 208a, 208b, 508a, 508b can comprise a respective vacuum nozzle 202a, 202b, 502a, 502b and a respective actuation subassembly 205a, 205b, 505a, 505b. In these aspects, each of the vacuum nozzles 202a, 202b, 502a, 502b can have a respective longitudinal axis 212a, 212b, 512 and a respective distal end 216a, 216b, 516a, 516b. In use, each vacuum nozzle 202a, 202b, 502a, 502b can be configured to apply suction to retain an object against the distal end 216a, 216b, 516a, 516b of the vacuum nozzle. In exemplary aspects, each vacuum nozzle 202a, 202b, 502a, 502b can be configured to apply a suction force that is at a sufficiently strong level to retain an embryo against the distal end 216a, 216b, 516a, 516b of the vacuum nozzle but at a sufficiently low level to avoid damage to the embryo. In another aspect, within each nozzle assembly 208a, 208b, 508a, 508b, the vacuum nozzle 202a, 202b, 502a, 502b is rotatable by the actuation subassembly 205a, 205b, 505a, 505b. In this aspect, the vacuum nozzles 202a, 202b, 502a, 502b of the first and second nozzle assemblies 208a, 208b, 508a, 508b are selectively rotatable to an object-transfer position in which the longitudinal axis of the first vacuum nozzle 202a, 502a is aligned with the longitudinal axis of the second vacuum nozzle 202b, 502b and the distal end 216a, 516a of the first vacuum nozzle is positioned proximate the distal end 216b, 516b of the second vacuum nozzle.

In exemplary aspects, each of the first and second vacuum nozzles 202a, 202b, 502a, 502b can be configured for compliant movement relative to its longitudinal axis. Optionally, in these aspects, the first and second vacuum nozzles 202a, 202b, 502a, 502b can be telescopic nozzles that are configured for "free" movement relative to their longitudinal axes. In use, the compliancy of the vacuum nozzles 202a, 202b, 502a, 502b can provide tolerance for engaging objects (e.g., embryos) as disclosed herein. For example, it is contemplated that the compliancy of the vacuum nozzles 202a, 202b, 502a, 502b can permit engagement of objects (e.g., embryos) when the objects are not positioned in an ideal (e.g., perfectly aligned) position for engagement.

In exemplary aspects, the vacuum nozzles 202a, 202b, 502a, 502b can comprise stainless steel. However, it is contemplated that other materials can be used. For example, in alternative aspects, it is contemplated that the vacuum nozzles 202a, 202b, 502a, 502b can comprise rubber suction cups.

In further aspects, the actuation subassembly 205a, 205b, 505a, 505b of each nozzle assembly 208a, 208b, 508a, 508b can comprise at least one rotational actuator coupled to the vacuum nozzle. Optionally, in these aspects, the at least one rotational actuator of each actuation subassembly 205a, 205b, 505a, 505b can comprise a plurality of rotational actuators that are configured to effect rotational movement of the nozzle assembly 208a, 208b, 508a, 508b relative to a plurality of rotational axes, such as for example, and without limitation, two, three, four, five, six, or more axes. In further aspects, the actuation subassembly 205a, 205b, 505a, 505b of each nozzle assembly 208a, 208b, 508a, 508b can further comprise at least one axial actuator configured to effect axial movement of the vacuum nozzle of the nozzle assembly relative to at least one axis.

In various aspects, and with reference to FIG. 9, the object orientation apparatus 200, 500 can further comprise at least one controller 800 that is communicatively coupled to the actuation subassemblies 205a, 205b, 505a, 505b of the first and second nozzle assemblies 208a, 208b, 508a, 508b. It is contemplated that the at least one controller 800 can be configured to control rotation of the vacuum nozzles 202a, 202b, 502a, 502b of the first and second nozzle assemblies 208a, 208b, 508a, 508b. In exemplary aspects, it is contemplated that the at least one controller of the object orientation apparatus 200, 500 can function as a central controller of each of the components of the system 100 disclosed herein. However, it is also contemplated that the disclosed object orientation apparatus 200, 500 can have its own dedicated controller that can optionally be positioned in communication with other controllers of the system 100.

In the object-transfer position, as shown in FIGS. 3B and 6B, the longitudinal axes of the first and second vacuum nozzles 202a, 202b, 502a, 502b can be substantially parallel to a transverse axis 240 that is perpendicular to a vertical axis. As used herein, the term "substantially parallel" refers to orientations in which the longitudinal axes of the first and second vacuum nozzles 202a, 202b, 502a, 502b are both within about 10 degrees of being parallel to the transverse axis 240. In exemplary aspects, the longitudinal axes of the first and second vacuum nozzles 202a, 202b, 502a, 502b can be parallel to the transverse axis 240.

More generally, in further exemplary aspects, in the object-transfer position, it is contemplated that the longitudinal axes of the first and second vacuum nozzles 202a, 202b, 502a, 502b can be positioned in any orientation in which the distal ends 216a, 216b, 516a, 516b of the first and second vacuum nozzles are positioned sufficiently close from one another to permit the transfer of an object (e.g., embryo) from one vacuum nozzle to the other vacuum nozzle. In these aspects, it is contemplated that the longitudinal axes of the first and second vacuum nozzles 202a, 202b, 502a, 502b can be positioned parallel to the transverse axis 240 or at any desired acute angle relative to the transverse axis 240.

Figure 6A:
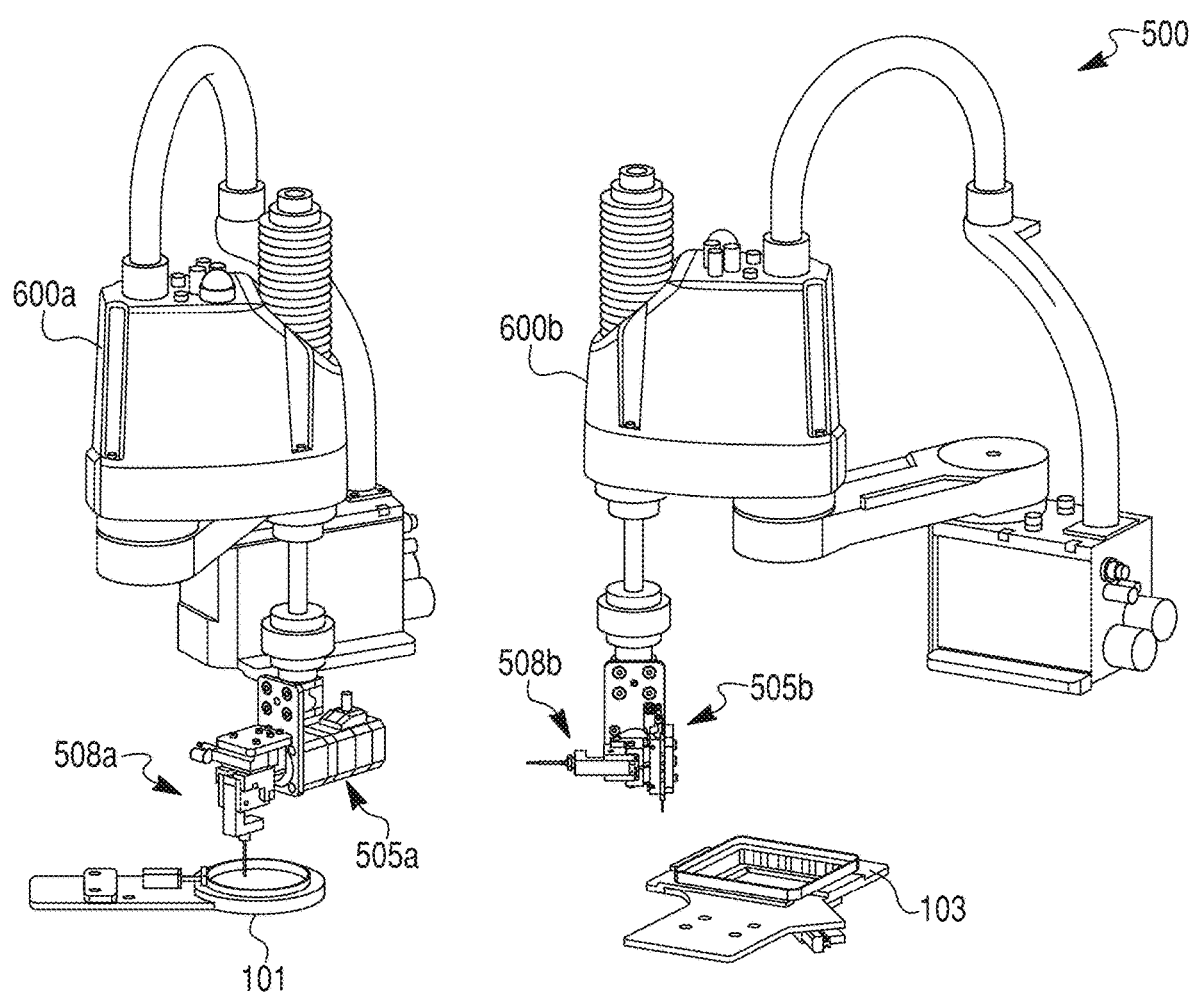
FIG. 6A is a top perspective view of an orientation apparatus having a pair of robots that are coupled to respective nozzle assemblies as disclosed herein. As shown, a first nozzle assembly can be used to retrieve an embryo from a first location (e.g., a petri dish).
Figure 6C:
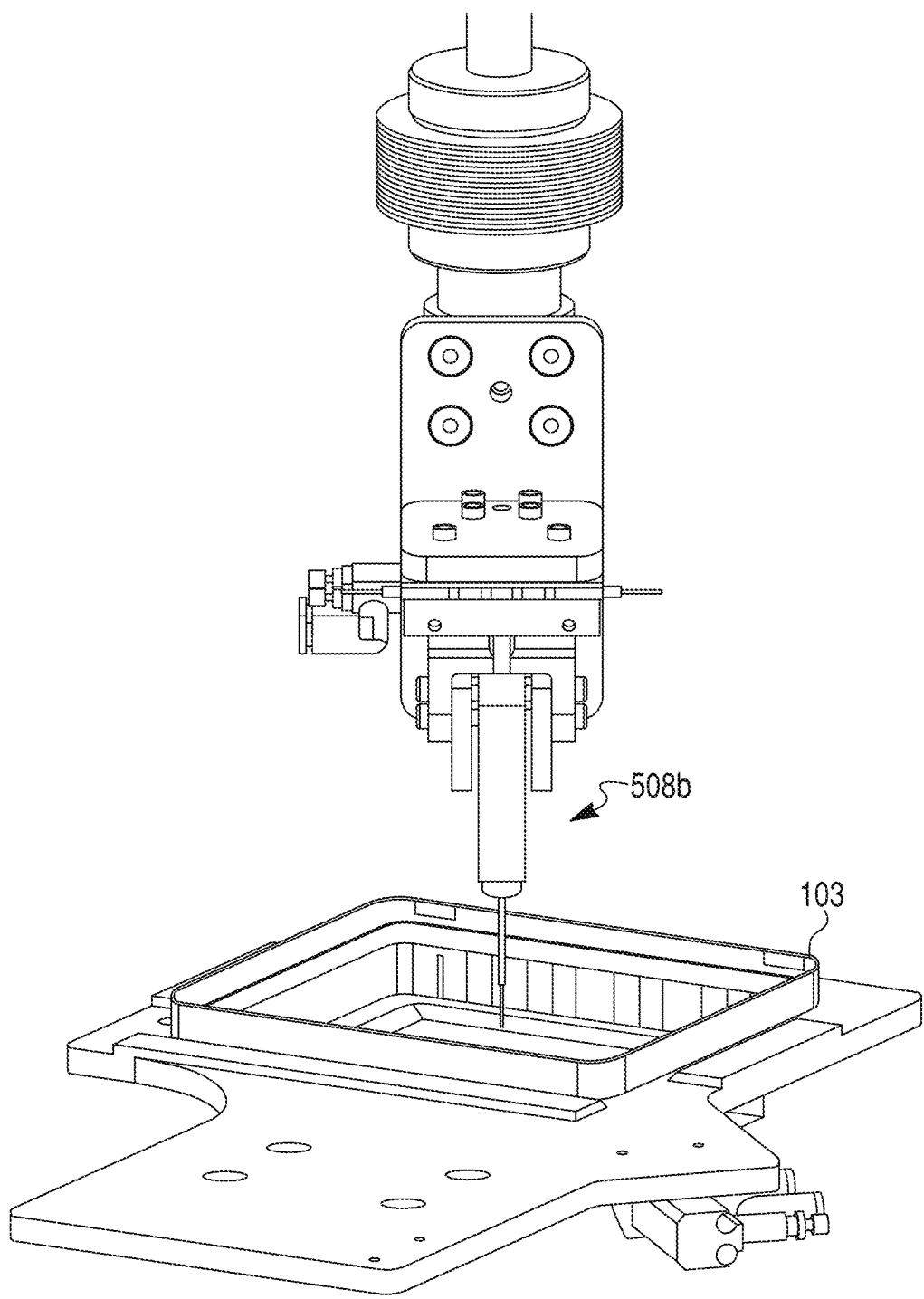
FIG. 6C is a close-up side perspective view depicting the second nozzle assembly releasing the embryo at a desired second location (e.g., into a growth medium within a tray).

In exemplary aspects, and as shown in FIGS. 3A, 6A, and 6C, the vacuum nozzles 202a, 202b, 502a, 502b of the first and second nozzle assemblies 208a, 208b, 508a, 508b can be selectively rotatable to respective object release/retrieval positions in which the vacuum nozzle of each vacuum nozzle assembly is angled downwardly from the transverse axis 240. Optionally, in the object release/retrieval position of each of the vacuum nozzle assemblies 208a, 208b, 508a, 508b, the longitudinal axis of the vacuum nozzle 202a, 202b, 502a, 502b is positioned at a selected acute angle relative to the transverse axis 240. Alternatively, in the object release/retrieval position of each of the vacuum nozzle assemblies 208a, 208b, 508a, 508b, the longitudinal axis of the vacuum nozzle 202a, 202b, 502a, 502b can be perpendicular to the transverse axis 240.

Figure 4A:
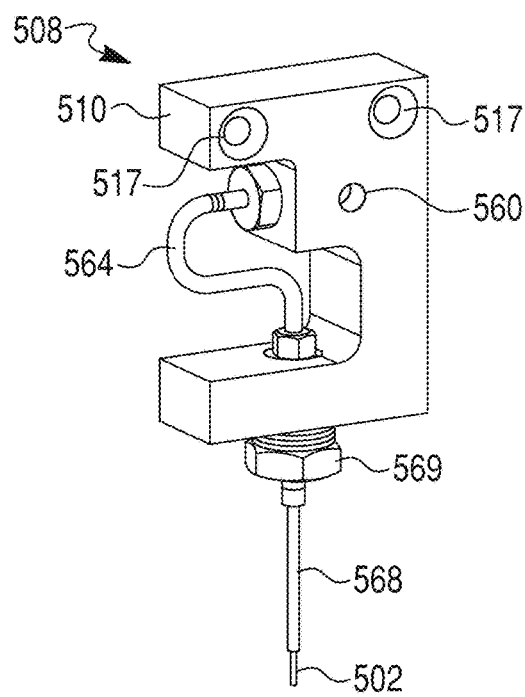
FIG. 4A is an isolated side perspective view of an exemplary nozzle assembly having a cartridge as disclosed herein.
Figure 4B:
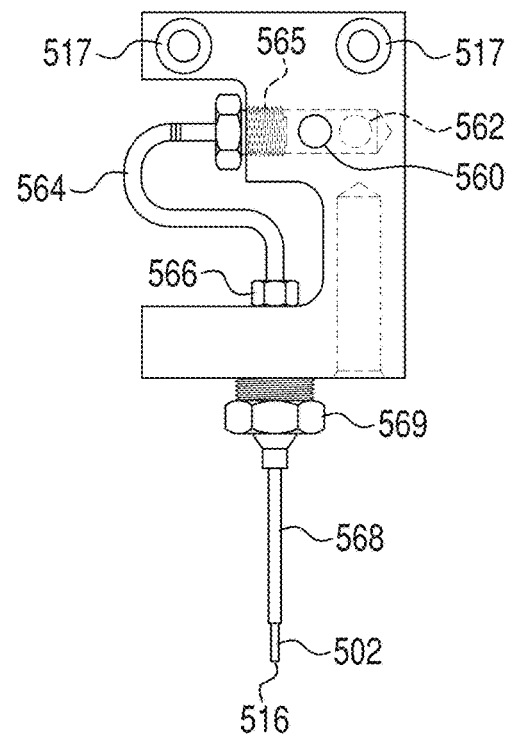
FIG. 4B is a partially transparent side elevational view of the nozzle assembly of FIG. 4A.

Optionally, in exemplary aspects and as shown in FIGS. 4A-6C, each nozzle assembly 508a, 508b can further comprise a cartridge 510a, 510b that is configured to selectively engage the vacuum nozzle 502a, 502b of the nozzle assembly such that movement of the cartridge imparts a corresponding movement to the vacuum nozzle. In these aspects, a portion of the cartridge 510a, 510b can be selectively engageable by the actuation subassembly 505 of the nozzle assembly 508a, 508b. Optionally, in additional aspects, each nozzle assembly 508a, 508b can further comprise a guide tube 568 that has a proximal portion 569 with an at least partially threaded outer surface and is configured to receive a portion of the vacuum nozzle 502a, 502b of the nozzle assembly 508a, 508b. In these aspects, the cartridge 510a, 510b can define a first threaded bore that is configured to threadedly engage the threaded outer surface of the guide tube 568. Optionally, in further optional aspects, each nozzle assembly 508a, 508b can further comprise a vacuum tube 564. In these aspects, the cartridge 510a, 510b can define a vacuum port 560 configured to receive suction from a vacuum source. As shown in FIGS. 4A-4B, the vacuum tube 564 can be positioned in communication with the vacuum port 560 and the guide tube 568 to provide suction to the vacuum nozzle 502a, 502b of the nozzle assembly 508a, 508b. In exemplary aspects, and as shown in FIG. 4B, it is contemplated that the vacuum tube 564 can optionally be provided with a proximal threaded portion 565 that is configured for receipt within a portion of the vacuum port 560. In further exemplary aspects, it is contemplated that each cartridge 510a, 510b can define a respective blow-off port 562. It is further contemplated that the vacuum port 560 and the blow-off port 562 can both be positioned in fluid communication with the vacuum tube 564. In use, the vacuum port can be positioned in fluid communication with a positive pressure source to thereby permit application of positive pressure through the vacuum tube and the vacuum nozzle. In exemplary aspects, the application of positive pressure through the blow-off port 562 (and the vacuum tube 564 and the nozzle 502a, 502b) can ensure that an object retained by the nozzle is released from the nozzle. It is further contemplated that the blow-off port 562 can be provided at an interior location relative to the vacuum port 560 to ensure that positive pressure applied through the blow-off port 562 can remove all contaminants from within the cartridge assembly. Optionally, in further exemplary aspects, it is contemplated that the cartridge 510a, 510b can be shaped to leave at least a portion of the vacuum tube 564 exposed and accessible from outside the cartridge. In these aspects, it is contemplated that a distal portion of the vacuum tube 564 can be coupled to a collar 566, with the vacuum tube 564 having a shape and/or curvature that is configured to bias the collar 566 (e.g., through a spring force) to a bottomed-out position in which the collar abuts the proximal portion 569 as shown in FIGS. 4A-4B.

Figure 5A:
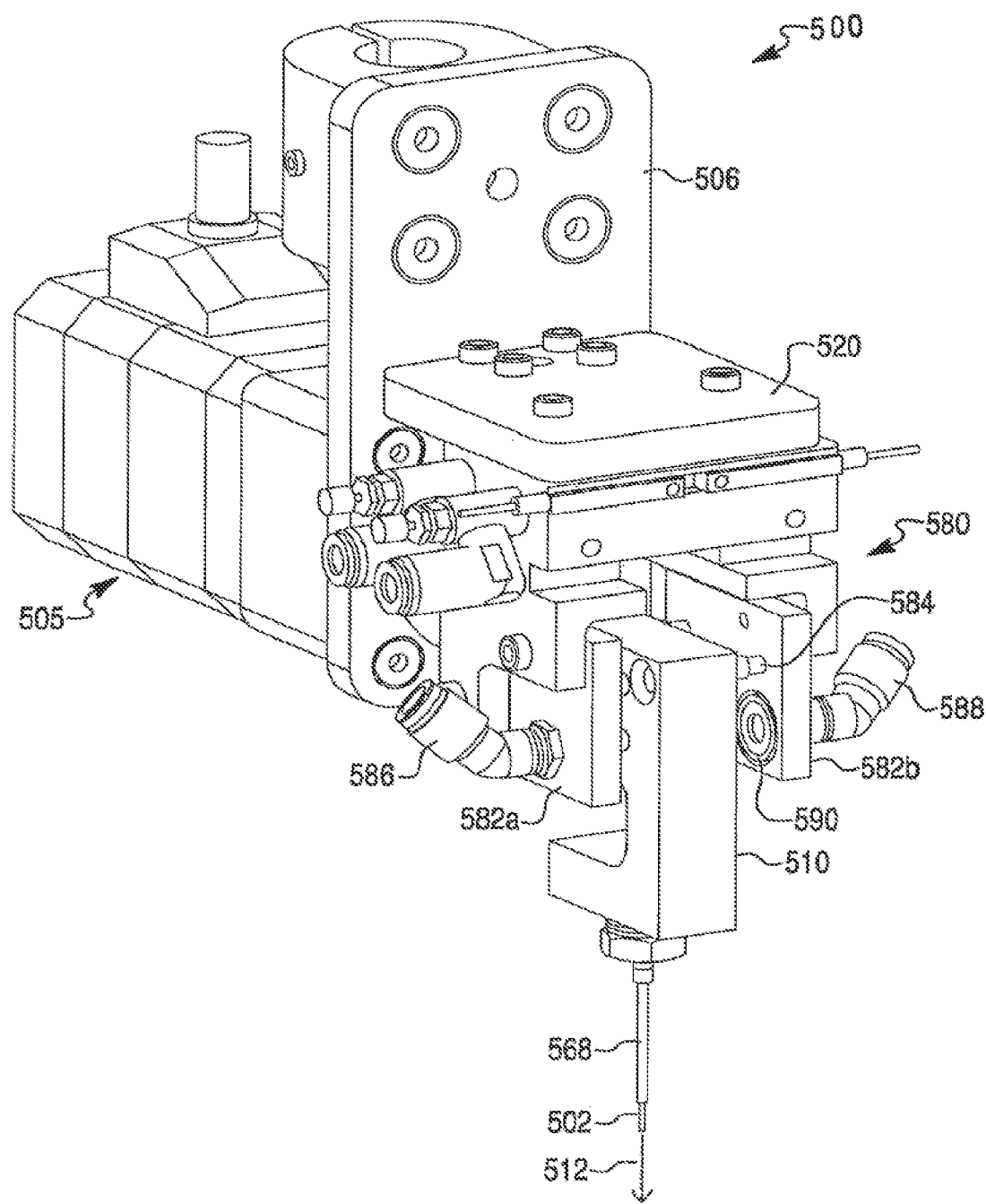
FIG. 5A is a top perspective view of an exemplary orientation apparatus as disclosed herein. As shown, the orientation apparatus can comprise an actuation subassembly, a cartridge for engaging a vacuum nozzle, and a cartridge gripper as disclosed herein.
Figure 5B:
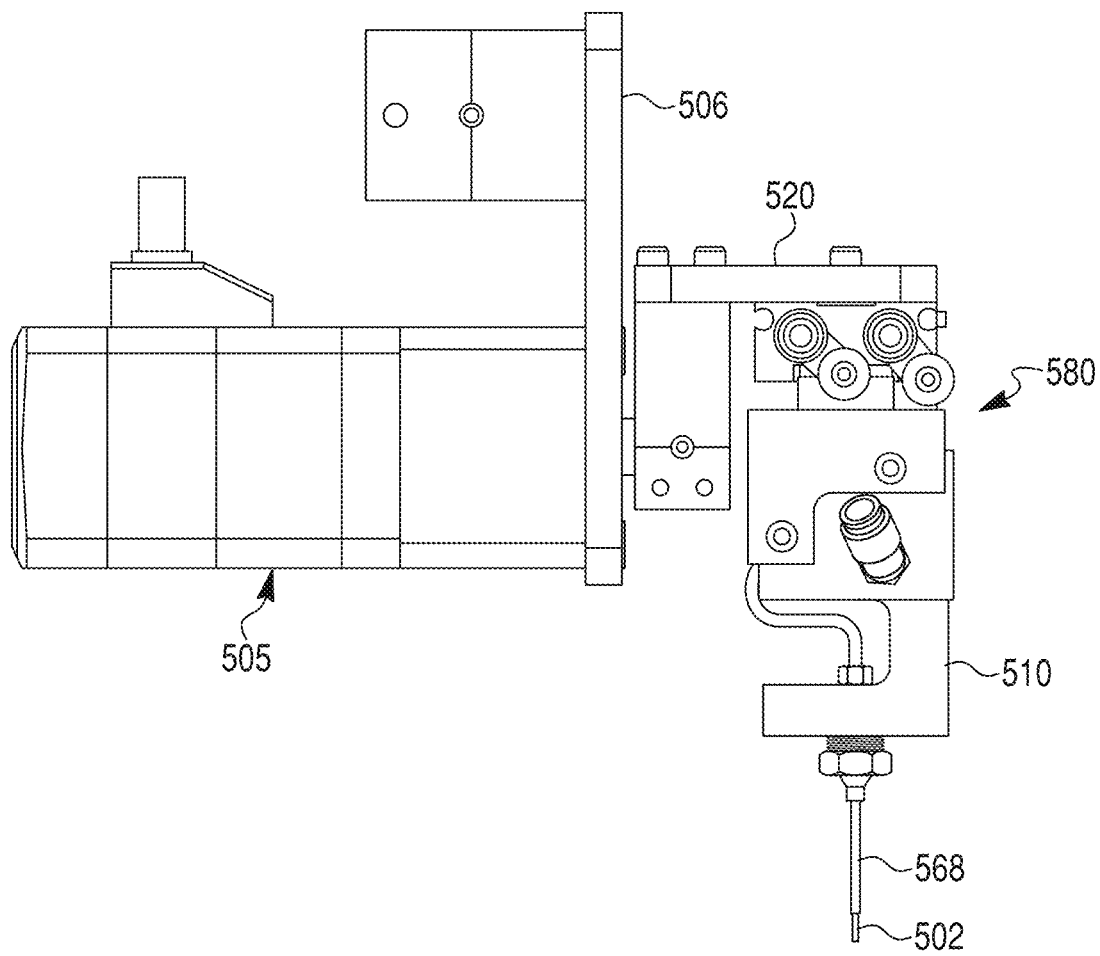
FIG. 5B is a side elevational view of the orientation apparatus of FIG. 5A.

In further exemplary aspects, and with reference to FIGS. 5A-5B, each actuation subassembly 505 can comprise a cartridge gripper 580 that is configured to selectively engage a proximal (top) portion of a respective cartridge 510a, 510b. In these aspects, the cartridge gripper 580 can comprise a pair of opposed panels 582a, 582b that are moveable toward and away from each other relative to an axis parallel to the transverse axis 240, to and from an engaged position (to engage the cartridge) and a disengaged position (no contact with the cartridge). Each panel 582a, 582b can define respective locating pins 584 that are configured for engagement with corresponding alignment recesses 517 defined in the proximal portion of the cartridge 510a, 510b. The first panel 582a can define a blow-off fitting 586 and corresponding opening that is configured for communication with the blow-off port 562 of the cartridge, and the second panel can define a vacuum fitting 588 and corresponding opening that is configured for communication with the vacuum port 560 of the cartridge. The openings for the vacuum fitting 588 and the blow-off fitting 586 can be provided with suitable sealing members 590. In use, the actuation subassembly 505 can selectively move the panels 582a, 582b about and between the engaged and disengaged positions. Thus, it is contemplated that one cartridge can be exchanged (e.g., automatically exchanged) for another cartridge if desired. It is further contemplated that cartridges can be exchanged as needed to account for damage to cartridge/nozzle components and/or to permit periodic sterilization of used cartridges.

Optionally, in exemplary aspects, and as shown in FIG. 6A, the object orientation apparatus 500 can further comprise first and second robots 600a, 600b. In these aspects, it is contemplated that the first robot 600a can have an arm coupled to the first nozzle assembly 508a and the second robot 600b can have an arm coupled to the second nozzle assembly 508b. It is further contemplated that the arm of the first robot 600a can be configured for selective movement to impart corresponding movement to the first nozzle assembly 508a and that the arm of the second robot 600b can be configured for selective movement to impart corresponding movement to the second nozzle assembly 508b. It is further contemplated that the first and second robots 600a, 600b can be communicatively coupled to the at least one controller 800. It is contemplated that the at least one controller 800 that is coupled to the first and second robots 600a, 600b can function as a central controller of each of the components of the system 100 disclosed herein. However, it is also contemplated that the disclosed robots 600a, 600b can have their own dedicated controller(s) that can optionally be positioned in communication with other controllers of the system 100. In exemplary aspects, the robots disclosed herein can be configured for rotational and/or axial movement relative to a plurality of axes, such as, for example and without limitation, six axes. Optionally, in these aspects, it is contemplated that the robots can comprise a Selective Compliance Assembly Robot Arm (SCARA) apparatus as is known in the art, such as SCARA robots manufactured by Epson Robots (Carson, CA).

Alternatively, in other optional aspects, and as shown in FIGS. 1-3B, the object orientation apparatus 200 can further comprise a base assembly 206. In these aspects, the first and second nozzle assemblies can be independently rotationally coupled to the base assembly. Optionally, as shown in FIG. 1, it is contemplated that the object orientation apparatus 200 can further comprise a robot that is coupled to the base assembly 206.

In one aspect, the first nozzle assembly 208a can comprise a first plate 220a that is secured to the vacuum nozzle 202a and at least one rotational actuator of the first nozzle assembly and rotationally coupled to the base assembly 206 such that rotation of the first plate effects a corresponding rotation of the vacuum nozzle. In this aspect, the second nozzle assembly 208b can comprise a second plate 220b that is secured to the vacuum nozzle 202b and at least one rotational actuator of the second nozzle assembly and rotationally coupled to the base assembly 206 such that rotation of the second plate effects a corresponding rotation of the second vacuum nozzle.

In another aspect, the base assembly 206 can comprise a transverse arm 244 and first and second nozzle assembly supports 242a, 242b that are slidably coupled to the transverse arm. In this aspect, the first plate 220a can be rotationally coupled to the first nozzle assembly support 242a, and the second plate 220b can be rotationally coupled to the second nozzle assembly support 242b. It is further contemplated that the first and second nozzle assembly supports 242a, 242b can be selectively and independently moveable relative to the transverse axis 240 to move the vacuum nozzles 202a, 202b of the first and second nozzle assemblies 208a, 208b relative to the transverse axis. In a further aspect, the object orientation apparatus 200, 500 can further comprise first and second transverse actuators respectively secured to the first and second nozzle assembly supports 242a, 242b. In this aspect, the at least one controller 800 can be configured to control movement of the first and second nozzle assembly supports 242a, 242b relative to the transverse axis 240.

Figure 2B:
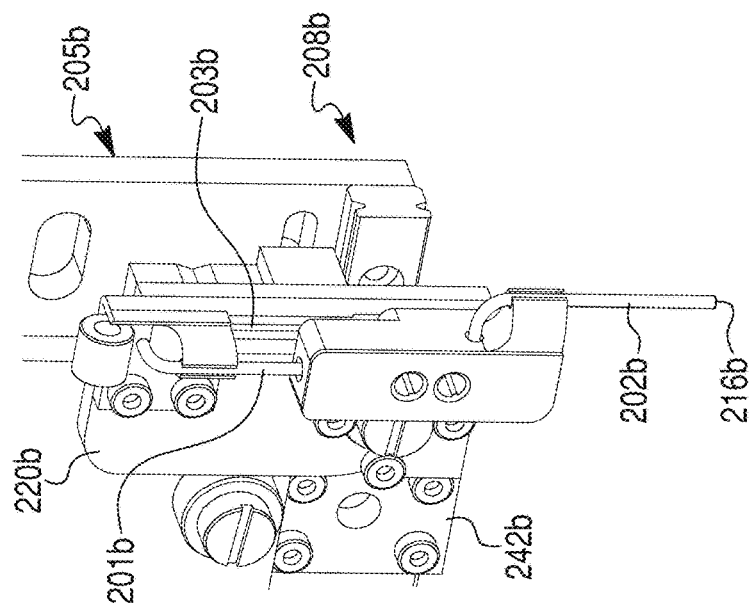
FIG. 2B is a close-up perspective view of an exemplary nozzle assembly as disclosed herein.
Figure 2A:
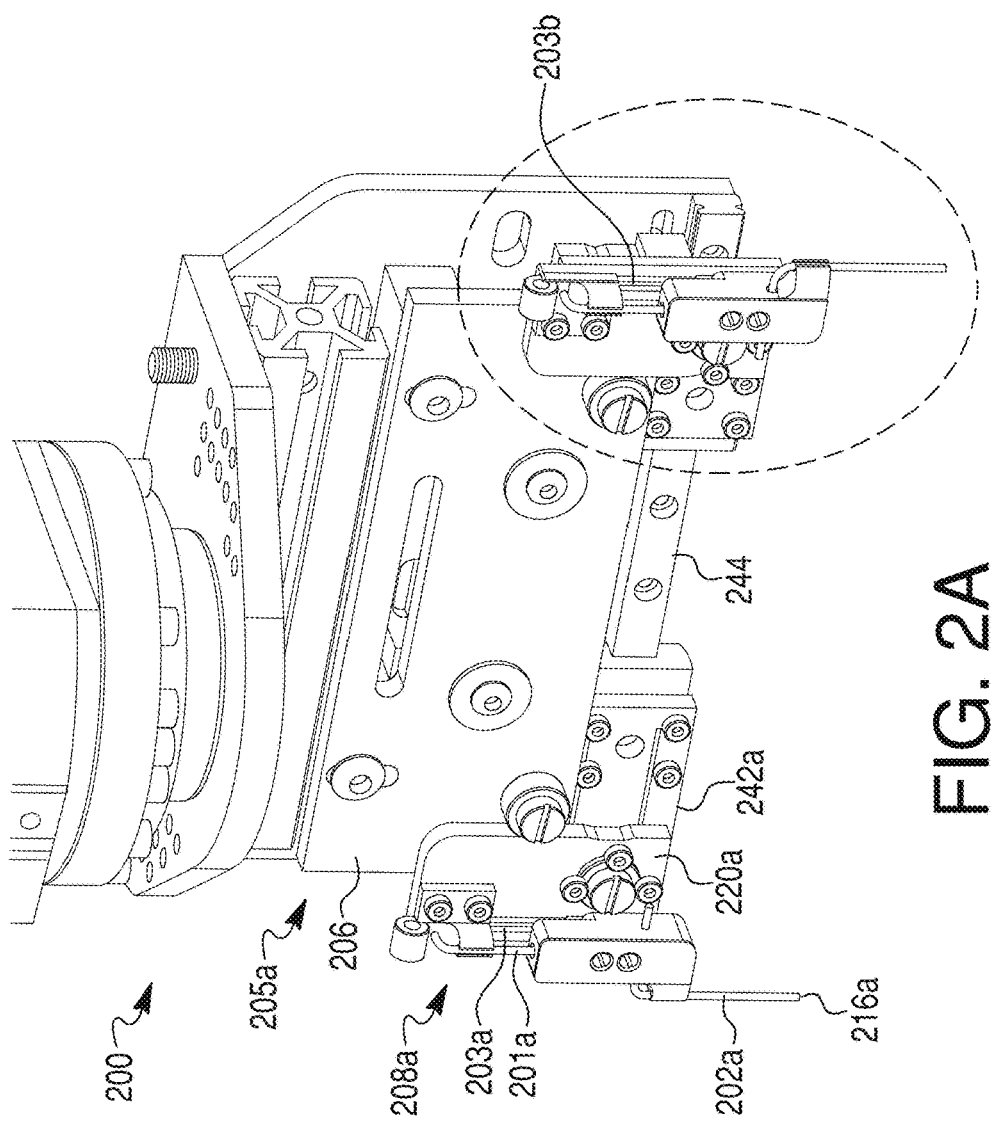
FIG. 2A is an isolated perspective view of an exemplary object orientation apparatus as disclosed herein.

Optionally, in various aspects, it is contemplated that the vacuum nozzles 202a, 202b can be slidably coupled to the first and second plates 220a, 220b to thereby permit axial movement of the vacuum nozzles. In these aspects, it is contemplated that the plates 220a, 220b can define respective slide elements 203a, 203b that are coupled to the vacuum nozzles and permit axial movement of the vacuum nozzles relative to the support plates. As shown in FIGS. 2A-2B, the slide elements 203a, 203b can be oriented parallel to the longitudinal axes of the vacuum nozzles to permit compliant movement of the nozzles relative to their longitudinal axes. It is contemplated that the slide elements 203a, 203b can be configured to provide minimal inertial interference with axial movement of the vacuum nozzles. In further aspects, it is contemplated that the nozzle assemblies 208a, 208b can comprise an actuator 201a, 201b that is configured to effect axial movement of the vacuum nozzles 202a, 202b. Optionally, in these aspects, it is contemplated that the actuators 201a, 201b can comprise a blow down mechanism for delivering pressurized air. Alternatively, in other aspects, it is contemplated that the actuators 201a, 201b can comprise a pneumatic cylinder or other conventional mechanical actuator. As shown in FIGS. 2A-2B, it is contemplated that the vacuum nozzles 202a, 202b can have an elbow structure that is supported by a housing, with the housing being slidably coupled to the plates 220a, 220b.

In various exemplary aspects, the object orientation apparatus 200, 500 can further comprise at least one camera 107 positioned in communication with the at least one controller 800. In these aspects, the at least one camera 107 can be configured to produce at least one image of an object (e.g., embryo) retained by the vacuum nozzle 202a, 502a of the first nozzle assembly 208a, 508a. An exemplary side elevational view of an embryo held against the distal end of a vacuum nozzle is provided in FIG. 8B. In operation, the at least one controller 800 can be configured to determine an orientation of the object (e.g., embryo) based upon the at least one image produced by the at least one camera. It is contemplated that the at least one controller 800 can use conventional optical recognition techniques to evaluate the shape of the retained object to determine the orientation of the object. In exemplary aspects, the at least one controller can be configured to determine if the orientation of the object corresponds to a desired orientation of the object. In response to determining the orientation of the object does not correspond to the desired orientation, the at least one controller 800 can be configured to selectively activate the at least one rotational actuator of each actuation subassembly 205a, 205b, 505a, 505b to move the first and second vacuum nozzle assemblies 208a, 208b, 508a, 508b to the object-transfer positions. When the actuation subassemblies 205a, 205b, 505a, 505b of the nozzle assemblies 208a, 208b, 508a, 508b also comprise at least one linear (axial) actuator configured to effect axial movement of the vacuum nozzle 202a, 202b, 502a, 502b of the nozzle assembly relative to at least one axis, the controller can be configured to selectively activate the at least one axial actuator of each actuation subassembly to move the first and second vacuum nozzle assemblies to the object-transfer positions.

In various aspects, the object orientation apparatus can further comprise at least one vacuum source positioned in communication with the at least one controller 800 and the vacuum nozzles 202a, 202b, 502a, 502b of the first and second nozzle assemblies 208a, 208b, 508a, 508b. In these aspects, the at least one controller 800 can be configured to selectively and independently adjust the application of vacuum force to the vacuum nozzles 202a, 202b, 502a, 502b of the first and second nozzle assemblies 208a, 208b, 508a, 508b. In further aspects, the object orientation apparatus can further comprise at least one positive pressure source positioned in communication with the at least one controller 800 and the vacuum nozzles 202a, 202b, 502a, 502b of the first and second nozzle assemblies 208a, 208b, 508a, 508b. In these aspects, the at least one controller 800 can be configured to selectively and independently adjust the application of positive to the vacuum nozzles 202a, 202b, 502a, 502b of the first and second nozzle assemblies 208a, 208b, 508a, 508b.

In exemplary aspects, the disclosed object orientation apparatus 200, 500 can be used in a method for positioning an object (e.g., an embryo) in a desired orientation. In these aspects, the method can comprise selectively activating the actuation subassembly of the first nozzle assembly to position the vacuum nozzle of the first nozzle assembly in the object release/retrieval position. In another aspect, the method can comprise applying suction through the vacuum nozzle of the first nozzle assembly to retain an object (e.g., embryo) against the distal end of the vacuum nozzle. In a further aspect, the method can comprise producing an image of the object (e.g., embryo) using the camera. In still another aspect, the method can comprise determining an orientation of the object (e.g., embryo) using the controller.

In exemplary aspects, the method can further comprise using the controller to compare the orientation of the object (e.g., embryo) to a desired orientation of the object (e.g., embryo). In response to determining that the orientation of the object corresponds to the desired orientation, the controller can selectively activate at least one actuator of the actuation subassembly of the first nozzle assembly to return the first nozzle assembly to the object release/retrieval position. Optionally, with the first nozzle assembly in the object release/retrieval position, the controller can cause the vacuum source to cease application of suction. In conjunction with ceasing application of suction, the controller can also activate a positive pressure source to apply positive pressure through the vacuum nozzle of the first nozzle assembly to ensure that the object is detached from the distal end of the vacuum nozzle and delivered to a selected location, such as, for example, growth media. In response to determining that the orientation of the object (e.g., embryo) does not correspond to the desired orientation, the controller can selectively activate at least one actuator of the actuation subassemblies of the first and second nozzle assemblies to move the first and second nozzle assemblies to the object-transfer position. With the first and second nozzle assemblies in the object-transfer position, the controller can: activate a vacuum source to apply suction through the vacuum nozzle of the second nozzle assembly to retain the object (e.g., embryo) against the distal end of the vacuum nozzle of the second nozzle assembly; and activate a positive pressure source to apply positive pressure through the vacuum nozzle of the first nozzle assembly to detach the object from the distal end of the vacuum nozzle of the first nozzle assembly. More specifically, with the first and second nozzle assemblies in the object-transfer position and the object retained against the distal end of the first nozzle assembly, the controller can initially activate a vacuum source to apply negative pressure through the vacuum nozzle of the second nozzle assembly and also, either concurrently or shortly thereafter, cause a vacuum source to cease application of negative pressure through the first nozzle assembly. Next, the controller can activate a positive pressure source to apply positive pressure through the vacuum nozzle of the first nozzle assembly as the second nozzle assembly is moved away from the object-transfer position. It is contemplated that the positive pressure applied through the vacuum nozzle can be sufficient to completely eliminate any negative pressure within the vacuum tube and/or nozzle assembly while remaining low enough to avoid disturbance of objects (e.g., embryos) that have already been placed in a desired location (e.g., growth media) as further disclosed herein. With the object retained against the distal end of the vacuum nozzle of the second nozzle assembly, the controller can selectively activate at least one actuator of the actuation subassembly of the second nozzle assembly to move the second nozzle assembly to the object release/retrieval position. With the second nozzle assembly in the object release/retrieval position, the controller can cause the vacuum source to cease application of suction. In conjunction with ceasing application of suction, the controller can also activate a positive pressure source to apply positive pressure through the vacuum nozzle of the first nozzle assembly to ensure that the object is detached from the distal end of the vacuum nozzle and delivered to a selected location, such as, for example, growth media.

IV. Systems and Methods of Singulating and Adjusting the Orientation of Extracted Embryos or Other Objects In exemplary aspects, and with reference to FIGS. 1, 6A-6C, 8A, and 9, it is contemplated that the disclosed singulation apparatus 300 and the disclosed object orientation apparatus 200, 500 can be provided together as part of a system 100. As shown in FIG. 1, in addition to the singulation apparatus 300 and the object orientation apparatus 200, 500, the system 100 can further comprise petri dish assemblies 101, 102, growth containers (e.g., STERIVENT tray assemblies manufactured by Duchefa Biochemie) 103, 104, a background screen 105, at least one plating station 106, and a camera 107. In exemplary aspects, it is contemplated that the robots disclosed herein can be configured to selectively control movement of the petri dishes and growth containers to various locations within the system, including, for example and without limitation, a lid removal station, an inspection/plating station, and an input/output stacking station. The at least one controller 800 of the system 100 can comprise additional cameras and/or optical/visualization equipment as required to permit analysis and identification of selected characteristics of embryos positioned within the petri dishes and growth containers within the system. In exemplary aspects, these cameras and/or optical/visualization equipment can provide information that the controller 800 can use to determine appropriate movements of the robots within the system. For example, if the cameras and/or optical visualization equipment identifies embryos in a petri dish that have selected characteristics, the robot can be activated to retrieve those selected embryos from the petri dish and transfer the embryos to a second location for further processing.

In exemplary aspects, and with reference to FIGS. 6A-6C, it is contemplated that embryos can first enter the system 100 by being placed directly within a singulation apparatus 300 as disclosed herein or by being positioned within a petri dish that is provided to the system.

In exemplary aspects, the petri dish can contain selection media, such as, for example and without limitation, a selection medium useful in a conventional doubled haploid process. In these aspects, it is contemplated that the double haploid process can optionally be used in conjunction with plant breeding process as are known in the art. Optionally, the selection medium can comprise an antimitoticor chromosome doubling agent (e.g., colchicine, oryzalin, or trifluralin) as is known in the art. It is contemplated that the placement of an embryo in the doubling media can cause the doubling of the chromosomes of the embryo. After identification of the doubled haploids using conventional camera and visualization systems, the doubled haploids can be selectively transferred from the petri dish to a growth container (e.g., a STERIVENT tray assembly) as disclosed herein, and germination can begin.

FIG. 6A depicts the initial step of transferring an embryo from a petri dish to a growth container, such as, for example and without limitation, a STERIVENT tray assembly. It is contemplated that a similar process can be followed to transfer a singulated embryo from a singulation apparatus as disclosed herein to a growth container. In either case, the growth container can comprise a selected growth medium. It is contemplated that an embryo positioned in the growth medium as disclosed herein can be used in plant breeding as is known in the art. Generally, in aspects, it is contemplated that following positioning of the embryo into or onto the growth medium, the resulting tissue can be used in plant breeding applications as are known in the art.

Following removal of the lid of a selected petri dish (in the case of embryos plated on a petri dish) or following singulation (in the case of embryos positioned on the screen of a simulation apparatus), the at least one controller 800 can determine the locations of the embryos that are to be transferred to a second location (e.g., a culture container) and selectively control movement of the first nozzle assembly to engage a selected embryo. Following engagement with the selected embryo, the at least one controller can determine the orientation of the engaged embryo and transfer the engaged embryo to a second nozzle assembly (FIG. 6B) as appropriate. As shown in FIG. 6C, when the embryo is positioned in the correct orientation for growth, the at least one controller can effect movement of the appropriate nozzle assembly to place the embryo in a desired location within the growth media of a culture container.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

The invention claimed is:

1. An object orientation apparatus comprising:
   first and second nozzle assemblies, wherein each of the first and second nozzle assemblies comprises a respective vacuum nozzle and a respective actuation subassembly, each of the vacuum nozzles having a respective longitudinal axis and distal ends, wherein each vacuum nozzle is configured to apply suction to retain an object against the distal end of the vacuum nozzle, and wherein within each nozzle assembly, the vacuum nozzle is rotatable by the actuation subassembly,
   wherein the vacuum nozzles of the first and second nozzle assemblies are selectively rotatable to an object-transfer position in which the longitudinal axis of the first vacuum nozzle is aligned with the longitudinal axis of the second vacuum nozzle and the distal end of the first vacuum nozzle is positioned proximate the distal end of the second vacuum nozzle.

2. The object orientation apparatus of claim 1, wherein each of the first and second vacuum nozzles is configured for compliant movement relative to its longitudinal axis.

3. The object orientation apparatus of claim 2, wherein the actuation subassembly of each nozzle assembly comprises at least one rotational actuator coupled to the vacuum nozzle, and wherein the object orientation apparatus further comprises at least one controller that is communicatively coupled to the actuation subassemblies of the first and second nozzle assemblies, wherein the at least one controller is configured to control rotation of the vacuum nozzles of the first and second nozzle assemblies.

4. The object orientation apparatus of claim 3, wherein in the object-transfer position, the longitudinal axes of the first and second vacuum nozzles are parallel to a transverse axis that is perpendicular to a vertical axis.

5. The object orientation apparatus of claim 4, wherein the vacuum nozzles of the first and second nozzle assemblies are selectively rotatable to respective object release/retrieval positions in which the vacuum nozzle of each vacuum nozzle assembly is angled downwardly from the transverse axis.

6. The object orientation apparatus of claim 5, wherein in the object release/retrieval position of each of the vacuum nozzles, the longitudinal axis of the vacuum nozzle is positioned at a selected acute angle relative to the transverse axis.

7. The object orientation apparatus of claim 5, wherein in the object release/retrieval position of each of the vacuum nozzles, the longitudinal axis of the vacuum nozzle is perpendicular to the transverse axis.

8. The object orientation apparatus of claim 3, wherein the at least one rotational actuator of each actuation subassembly comprises a plurality of rotational actuators that are configured to effect rotational movement of the nozzle assembly relative to a plurality of rotational axes.

9. The object orientation apparatus of claim 3, wherein the actuation subassembly of each nozzle assembly further comprises at least one axial actuator configured to effect axial movement of the vacuum nozzle of the nozzle assembly relative to at least one axis.

10. The object orientation apparatus of claim 3, wherein each nozzle assembly further comprises a cartridge that is configured to selectively engage the vacuum nozzle of the nozzle assembly such that movement of the cartridge imparts a corresponding movement to the vacuum nozzle, and wherein a portion of the cartridge is selectively engageable by the actuation subassembly of the nozzle assembly.

11. The object orientation apparatus of claim 10, wherein each nozzle assembly further comprises a guide tube that is configured to receive a portion of the vacuum nozzle of the nozzle assembly.

12. The object orientation apparatus of claim 11, wherein each nozzle assembly further comprises a vacuum tube, wherein the cartridge defines a vacuum port configured to receive suction from a vacuum source and a blow-off port configured to receive positive pressure from a positive pressure source, and wherein the vacuum tube is positioned in communication with the vacuum port, the blow-off port, and the guide tube to provide suction and positive pressure to the vacuum nozzle of the nozzle assembly.

13. The object orientation apparatus of claim 3, further comprising:
   a first robot having an arm coupled to the first nozzle assembly, wherein the arm of the first robot is configured for selective movement to impart corresponding movement to the first nozzle assembly; and
   a second robot having an arm coupled to the second nozzle assembly, wherein the arm of the second robot is configured for selective movement to impart corresponding movement to the second nozzle assembly.

14. The object orientation apparatus of claim 13, wherein the first and second robots are communicatively coupled to the at least one controller.

15. The object orientation apparatus of claim 3, further comprising a base assembly, wherein the first and second nozzle assemblies are rotationally coupled to the base assembly.

16. The object orientation apparatus of claim 3, further comprising at least one camera positioned in communication with the at least one controller, wherein the at least one camera is configured to produce at least one image of an object retained by the vacuum nozzle of the first nozzle assembly.

17. The object orientation apparatus of claim 16, wherein the at least one controller is configured to determine an orientation of the object based upon the at least one image produced by the at least one camera.

18. The object orientation apparatus of claim 17, wherein the at least one controller is configured to determine if the orientation of the object corresponds to a desired orientation of the object.

19. The object orientation apparatus of claim 18, wherein, in response to determining the orientation of the object does not correspond to the desired orientation, the at least one controller is configured to selectively activate the at least one rotational actuator of each actuation subassembly to move the first and second vacuum nozzle assemblies to the object-transfer positions.

20. The object orientation apparatus of claim 19, wherein the actuation subassembly of each nozzle assembly comprises at least one axial actuator configured to effect axial movement of the vacuum nozzle of the nozzle assembly relative to at least one axis, and wherein the controller is configured to selectively activate the at least one axial actuator of each actuation subassembly to move the first and second vacuum nozzle assemblies to the object-transfer positions.

21. A method of positioning an object in a desired orientation comprising:

providing first and second nozzle assemblies, wherein each of the first and second nozzle assemblies comprises a respective vacuum nozzle and a respective actuation subassembly, each of the vacuum nozzles having a respective longitudinal axis and distal ends, wherein each vacuum nozzle is configured to apply suction to retain an object against the distal end of the vacuum nozzle, and wherein within each nozzle assembly, the vacuum nozzle is rotatable by the actuation subassembly, wherein the vacuum nozzles of the first and second nozzle assemblies are selectively rotatable to an object-transfer position in which the longitudinal axis of the first vacuum nozzle is aligned with the longitudinal axis of the second vacuum nozzle and the distal end of the first vacuum nozzle is positioned proximate the distal end of the second vacuum nozzle;

selectively activating at least one actuator of the actuation subassembly of the first nozzle assembly to position the first nozzle assembly in the object release/retrieval position;

activating a vacuum source to apply suction through the vacuum nozzle of the first nozzle assembly to retain an object against the distal end of the vacuum nozzle of the first nozzle assembly;

producing an image of the object using the camera; and determining an orientation of the object using the controller.

22. The method of claim 21, further comprising using the controller to compare the orientation of the object to a desired orientation of the object.

23. The method of claim 22, wherein, in response to determining that the orientation of the object corresponds to the desired orientation, the controller selectively activates at least one actuator of the actuator subassembly of the first nozzle assembly to return the first nozzle assembly to the object release/retrieval position.

24. The method of claim 23, wherein, with the first nozzle assembly in the object release/retrieval position, the controller activates a positive pressure source to apply positive pressure through the vacuum nozzle of the first nozzle assembly to detach the object from the distal end of the vacuum nozzle of the first nozzle assembly.

25. The method of claim 22, wherein, in response to determining that the orientation of the object does not correspond to the desired orientation, the controller selectively activates at least one actuator of the actuation subassemblies of the first and second nozzle assemblies to move the first and second nozzle assemblies to the object-transfer position.

26. The method of claim 25, wherein, with the first and second nozzle assemblies in the object-transfer position, the controller:

activates a positive pressure source to apply positive pressure through the vacuum nozzle of the first nozzle assembly to detach the object from the distal end of the vacuum nozzle of the first nozzle assembly; and activates a vacuum source to apply suction through the vacuum nozzle of the second nozzle assembly to retain the object against the distal end of the vacuum nozzle of the second nozzle assembly.

27. The method of claim 26, with the object retained against the distal end of the vacuum nozzle of the second nozzle assembly, the controller selectively activates at least one actuator of the actuation subassembly of the second nozzle assembly to move the second nozzle assembly to the object release/retrieval position.

28. The method of claim 27, wherein, with the second nozzle assembly in the object release/retrieval position, the controller activates a positive pressure source to apply positive pressure through the vacuum nozzle of the second nozzle assembly to detach the object from the distal end of the vacuum nozzle of the second nozzle assembly.

29. The method of claim 21, wherein the object is a plant embryo.

* * * * *